United States Patent [19]

Tschopp

[11] 4,324,898
[45] Apr. 13, 1982

[54] HETEROCYCLIC COMPOUNDS USEFUL AS COLOR PHOTOGRAPHIC MATERIAL

[75] Inventor: Paul Tschopp, Düdingen, Switzerland

[73] Assignee: Ciba Geigy AG, Basel, Switzerland

[21] Appl. No.: 71,329

[22] Filed: Aug. 30, 1979

Related U.S. Application Data

[62] Division of Ser. No. 895,579, Apr. 12, 1978, Pat. No. 4,206,278.

[30] Foreign Application Priority Data

Apr. 29, 1977 [CH] Switzerland ............... 5378/77

[51] Int. Cl.³ .................................. C07D 277/04
[52] U.S. Cl. .................... 548/184; 260/326.85; 548/266; 548/222; 548/341; 548/185; 430/557; 430/558
[58] Field of Search ............ 548/190, 184, 185, 266, 548/222, 341; 260/326.85

[56] References Cited

U.S. PATENT DOCUMENTS

| | | | |
|---|---|---|---|
| 2,728,658 | 12/1955 | McCrossen et al. | 95/6 |
| 3,253,924 | 5/1966 | Loria et al. | 96/100 |
| 3,265,506 | 8/1966 | Weissberger et al. | 960/100 |
| 3,277,155 | 10/1966 | Loria et al. | 260/476 |
| 3,408,194 | 10/1968 | Loria | 96/100 |
| 3,447,928 | 6/1969 | Loria | 96/100 |
| 3,770,719 | 11/1973 | Fisher et al. | 548/190 |
| 3,770,727 | 11/1973 | Brack et al. | 548/190 |
| 3,816,391 | 6/1974 | Coates et al. | 548/190 |

FOREIGN PATENT DOCUMENTS

| | | |
|---|---|---|
| 1800420 | 10/1968 | Fed. Rep. of Germany . |
| 2057941 | 11/1970 | Fed. Rep. of Germany . |
| 2114577 | 3/1971 | Fed. Rep. of Germany . |
| 2163812 | 12/1971 | Fed. Rep. of Germany . |
| 2213461 | 3/1972 | Fed. Rep. of Germany . |
| 2219917 | 4/1972 | Fed. Rep. of Germany . |
| 2261361 | 12/1972 | Fed. Rep. of Germany . |
| 2318807 | 4/1973 | Fed. Rep. of Germany . |
| 2329587 | 6/1973 | Fed. Rep. of Germany . |
| 2414006 | 3/1974 | Fed. Rep. of Germany . |
| 2431480 | 7/1974 | Fed. Rep. of Germany . |
| 2433812 | 7/1974 | Fed. Rep. of Germany . |
| 2442703 | 9/1974 | Fed. Rep. of Germany . |
| 2528638 | 6/1975 | Fed. Rep. of Germany . |
| 869169 | 10/1941 | France . |
| 991453 | 6/1951 | France . |
| 1385596 | 7/1966 | France . |
| 638039 | 5/1950 | United Kingdom . |
| 953454 | 3/1964 | United Kingdom . |
| 1092506 | 11/1967 | United Kingdom . |

*Primary Examiner*—Nicholas S. Rizzo
*Attorney, Agent, or Firm*—Sprung, Felfe, Horn, Lynch & Kramer

[57] ABSTRACT

Color photographic material is provided which comprises at least one silver halide emulsion layer containing a yellow color coupler of the formula

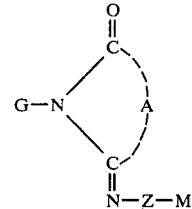

in which G represents a yellow coupler radical bonded via the active methine group to the heterocyclic ring, Z represents —CO— or —SO$_2$— and M represents a substituent and A represents the non-metallic atoms necessary to complete a five-membered saturated heterocyclic ring.

The new two-equivalent yellow couplers lead due to their improved reactivity (high maximum density), minimal fog and high fastness to light and outstanding spectral properties of the dyestuffs formed therefrom to a color photographic material of advantageous properties.

3 Claims, No Drawings

HETEROCYCLIC COMPOUNDS USEFUL AS COLOR PHOTOGRAPHIC MATERIAL

This is a division of application Ser. No. 895,579, filed Apr. 12, 1978, now U.S. Pat. No. 4,206,278.

In order to produce coloured photographic images, exposed silver halide emulsion layers, which at the same time contain colour couplers, are, as is known, developed with a developer substance which contains aromatic primary amino groups. The oxidised developer substance then reacts with the colour coupler with the formation of an image dye, the amount of the latter depending on the amount of incident light.

In general, a light-sensitive photographic multi-layer material is used which consists of a red-sensitive layer, which contains the cyan coupler, a green-sensitive layer, which contains the magenta coupler, and a blue-sensitive layer, which, in turn, contains the yellow coupler. On colour developing, the corresponding dyes having the colours cyan, magenta and yellow then form.

Usually, phenols or α-naphthols are employed as cyan couplers, pyrazolones are employed as magenta couplers and acylacetylamides are employed as yellow couplers. The dyes formed after developing are then indophenols, indamines or azomethines.

Conventional colour couplers possess an active methylene group, the conversion of which into the corresponding image dye requires four equivalents of silver halide; colour couplers of this type are therefore called four-equivalent couplers. Colour couplers in which one hydrogen atom of the active methylene group has been replaced by a group which is detachable during the coupling reaction are also known. In this case, two equivalents of silver halide are required to produce the corresponding image dye. Colour couplers of this type are therefore designated two-equivalent couplers.

Compared with the four-equivalent couplers, two-equivalent couplers are distinguished by the advantages given below:

1. The amount of silver halide required to form the same amount of dye is only half as great; as a result the production costs for a photographic material are noticeably reduced.
2. The light-sensitive layer can be kept thinner, as a result of which the sharpness and the resolution of the resulting coloured image are improved.
3. The sensitivity of the lower layers is increased as a result of the increased light transmission, since the thickness of the upper layers is reduced.

In the case of the yellow couplers, the leaving groups in two-equivalent couplers proposed to date are essentially those which follow: halogen atoms, as described, for example, in German Offenlegungschrift No. 2,114,577, French Patent Specification Nos. 991,453 and 869,169 or U.S. Pat. Nos. 2,728,658 and 3,277,155; the group —OR, in which R is alkyl, aryl, a heterocyclic radical or acyl, as described, for example, in British patent specification No. 1,092,506, French Patent Specification No. 1,385,696 or in U.S. Pat. Nos. 3,447,928 and 3,408,194; the —SR" group described in British patent specification No. 953,454 or U.S. Pat. No. 3,265,506; the 1,2,3-benztriazolyl group of the formula

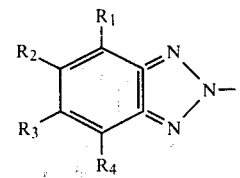

the radicals —SO₃H and —SCH (British patent specification No. 638,039 and U.S. Pat. No. 3,253,924) imide groups of the formulae

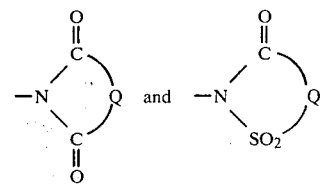

radicals of the formula

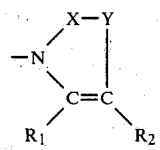

leaving groups of the formula

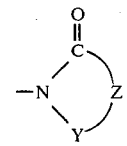

leaving groups of the formula

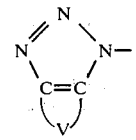

in which V together with the —C=C— grouping forms an aromatic ring of the benzene series or a heterocyclic ring containing at least one nitrogen atom (German Offenlegungsschrift No. 2,414,006) leaving groups of the formula

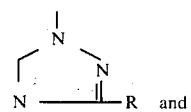

-continued

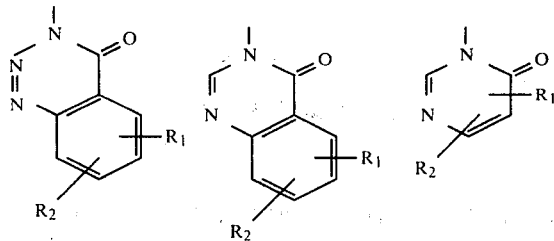

according to German Offenlegungsschrift No. 2,528,638 and in some cases according to German Offenlegungsschrift No. 2,442,703 leaving groups of the formula

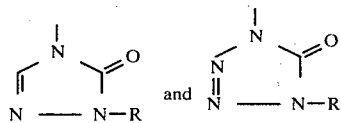

according to German Offenlegungsschrift No. 2,442,703 and specific pyridones and pyridazones according to German Offenlegungsschrift No. 2,318,807.

The object of the present invention is to provide readily accessible two-equivalent couplers, for materials for colour photography, which, compared with known two-equivalent couplers, are distinguished by improved reactivity (high maximum density) and minimal fogging and by the high fastness to light and the outstanding spectral properties of the dyes formed therefrom.

The invention relates to a colour photographic material, which comprises at least one silver halide emulsion layer which contains, as a yellow coupler, a compound of the formula

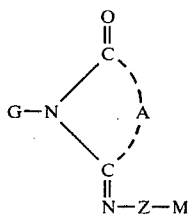

in which G represents a yellow coupler radical bonded via the active methine group to the heterocyclic ring, Z represents —CO— or —SO$_2$— and M represents a substituent and A represents the non-metallic atoms necessary to complete a five-membered saturated heterocyclic ring.

The invention also relates to a process for the production of a yellow image, which comprises exposing a material, for colour photography, which contains, on a base, at least one silver halide emulsion layer which contains, as a yellow coupler, at least one compound of the formula (1), and treating the exposed material with an aqueous alkaline solution which contains an aromatic amine as the developer.

The invention also relates to the yellow images produced by this process.

The invention also relates to the novel yellow couplers of the formula (1).

The radical M in the compounds of the formula (1) can be alkyl having 1 to 18 carbon atoms and these alkyl radicals can be straight-chain or branched, for example methyl, ethyl, n-propyl, iso-propyl, n-butyl, iso-butyl, tert.-butyl, amyl, n-hexyl and n-heptyl; and octyl, nonyl, decyl, dodecyl, tridecyl, tetradecyl, pentadecyl, hexadecyl, heptadecyl and octadecyl, the various isomers being included in each case.

These alkyl radicals can be substituted by halogen atoms, especially fluorine, chlorine, for example the radicals of the formulae —CH$_2$Cl or —CCl$_3$, or bromine; and also by hydroxyl, nitro or cyano; or alkoxy, especially having 1 to 5 carbon atoms in the alkoxy moiety, or aryloxy. Alkyl substituted by alkoxy or aryloxy can have, for example, the following formulae:
—CH$_2$—OC$_n$H$_{2n+1}$ (n is an integer from 1 to 5)

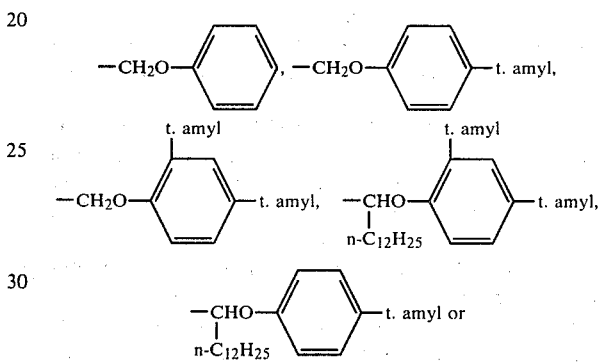

[t.amyl: —C(CH$_3$)$_2$(C$_2$H$_5$)]. The alkyl radicals can also be substituted by amino, for example NH$_2$ or —NHC$_n$H$_{2n+1}$ or —N(C$_n$H$_{2n+1}$)$_2$, in which n is 1 to 5. M can also be cycloalkyl, such as cycloalkyl having 1 to 4 cycloalkyl rings and 5 to 10 carbon atoms, for example cyclopentyl, cyclohexyl, norbornyl or 1-adamantyl; aralkyl, especially benzyl, or aryl, especially phenyl. Substituents on the phenyl ring can be: —C$_n$H$_{2n+1}$ or —O—C$_n$H$_{2n+1}$, in which n is 1 to 5, for example methyl, ethyl, propyl, butyl or amyl and isomeric radicals, or methoxy, ethoxy, propoxy, butoxy or pentoxy and isomeric radicals, or halogen, especially chlorine and bromine; acylamino, especially —NHCOC$_n$H$_{2n+1}$ and

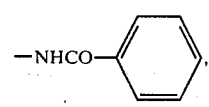

in which n is 1 to 5; SO$_3$H, sulphonamido groups, such as —SO$_2$NH$_2$, —SO$_2$N(C$_n$H$_{2n+1}$)$_2$ or —SO$_2$NH(C$_n$H$_{2n+1}$), —COOH, carboxamido groups, such as —CONH$_2$, —CON(C$_n$H$_{2n+1}$)$_2$ or —CONH(C$_n$H$_{2n+1}$), carbalkoxy groups, such as —COOC$_n$H$_{2n+1}$,

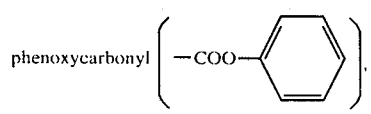

-continued benzyloxycarbonyl 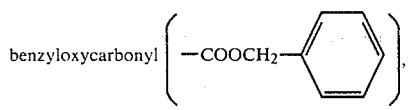

hydroxy, nitro, cyano, amino groups, such as —NH$_2$, —NHC$_n$H$_{2n+1}$ or —N(C$_n$H$_{2n+1}$)$_2$, or alkylmercapto, especially of the formula —SC$_m$H$_{m+1}$ (m=1 to 18).

Further substituents on the phenyl nucleus can be of the formula —SO$_2$E or —COE, in which E can be alkyl having 1 to 18 carbon atoms (as indicated above). The alkyl radicals E can be substituted by halogen, for example chlorine or bromine, nitro, cyano, amino or alkoxy having 1 to 18 carbon atoms; E can also be cycloalkyl, especially cyclohexyl, or aryl, especially phenyl and in some cases also substituted phenyl. Pyridyl, pyrimidyl, furyl or thienyl are further meanings for E. The radical M can also be pyridyl, furyl or thienyl, or perfluoroalkyl, especially a radical of the formula C$_n$F$_{2n+1}$. If Z is —CO—, M can be amino (—NH$_2$), mono- or dialkylamino, especially of the formulae —NHC$_n$H$_{2n+1}$ and —N(C$_n$H$_{2n+1}$)$_2$, alkoxy having 1 to 18 carbon atoms (—OC$_m$H$_{2m+1}$, m=1 to 18), or phenoxy

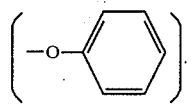

Furthermore, under the indicated condition (Z is —CO—), M can also be acyl, for example C$_n$H$_{2n+1}$CO— or

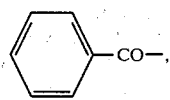

in which the phenyl ring can also contain further substituents. Furthermore, M can be carbalkoxy (—COOC$_n$H$_{2n+1}$) or carboxamide which is N-substituted or N,N-disubstituted by alkyl having 1 to 3 carbon atoms and/or phenyl

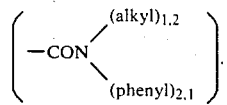

The index n is always 1 to 5.

The substituent G in the compounds of the formula (1) is a yellow coupler radical, especially an open-chain yellow coupler radical, bonded via the active methine group, i.e. the carbon atom bonded to the hetero-ring is not a constituent of a ring. Preferably, the substituent G is an acylacetic acid amide radical which is bonded via the α-carbon atom of the acetic acid group to the leaving group and in which acyl (Q—CO—) is in particular pivaloyl and substituted or unsubstituted benzoyl and amide is in particular anilide which is unsubstituted or substituted on the phenyl ring. Pivaloylacetanilide radicals are preferred.

The radical G can be represented by the formula

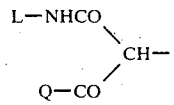

Acyl radicals (Q—CO—) can be those in which Q is alkyl having at most 32 carbon atoms, α-alkoxyalkyl having 2 to 32 carbon atoms, α-aryloxyalkyl having 7 to 40 carbon atoms, cycloalkyl having 1 to 4 cycloalkyl rings, or an aryl radical (preferably phenyl radical) or heterocyclic radical which is unsubstituted or further substituted by alkyl or alkoxy having 1 to 18 carbon atoms, halogen, such as chlorine or bromine, acylamino (especially derived from carboxylic acids), sulphonamide or carboxamide.

The aryl or heterocyclic radical can be substituted by one or more substituents.

Preferred radicals Q are tertiary butyl, norbornyl, [2,2,2]-bicyclooctyl, phenyl, 3,4-methylenedioxyphenyl, p-methoxyphenyl or 3-acylaminophenyl, or —HN—COR', (in which —COR' is acyl having 1 to 40 carbon atoms).

The phenyl ring (L) of the anilide can be substituted by one or more of the following substituents: halogen, such as chlorine or bromine, alkyl and alkoxy, especially having 1 to 5 carbon atoms, acylamino, preferably derived from carboxylic acids and having 1 to 40 carbon atoms, sulphonamide, carboxamide having 1 to 40 carbon atoms or carboxylic acid ester, especially a carboxylic acid alkyl ester having 2 to 40 carbon atoms.

The acylamino or carbox(sulphon)amido groups can also carry the ballast groups which are customary for colour couplers and are known per se, i.e. groups which impart to the coupler a good solubility in a high-boiling solvent (oil) customarily used for incorporating the coupler in the photographic material.

The radical A represents the non-metallic atoms necessary to complete a five-membered saturated heterocyclic ring. In particular A is the group —W—Y—, which is illustrated by the following formulae:

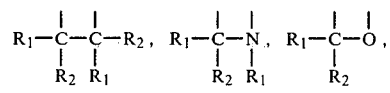

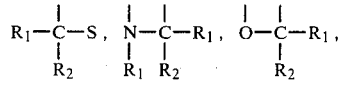

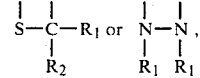

in which R$_1$ is hydrogen, alkyl having 1 to 18 carbon atoms, which is straight-chain or branched (as indicated for the radical M), aralkyl, especially benzyl, cycloalkyl, especially cyclohexyl or cyclopentyl, aryl, especially phenyl and naphthyl, or acyl, especially having 1 to 5, and preferably having 2 to 5, carbon atoms, for example CH$_3$CO—, CH$_3$CH$_2$CO—, CH$_3$(CH$_2$)$_2$CO— or CH$_3$(CH$_2$)$_3$CO—, and R$_2$ is alkyl, aralkyl or aryl (as indicated for R$_1$), or R$_1$ and R$_2$ together with the atom or atoms to which they are bonded can form a 4-membered to 6-membered ring. Preferred radicals R$_1$ are hydrogen, alkyl having 1 to 5 carbon atoms or phenyl and preferred radicals R$_2$ are alkyl having 1 to 5 carbon atoms, acyl having 1 to 5, and preferably having 2 to 5, carbon atoms, or phenyl.

The materials according to the invention, for colour photography, contain, as yellow couplers, in particular compounds of the formula (1) in which A is as defined, G is a yellow coupler radical bonded via the active methine group to the heterocyclic ring, Z is —CO— or —SO$_2$—, M is alkyl having 1 to 18 carbon atoms, which is unsubstituted or substituted by halogen, hydroxyl, nitro, cyano, alkoxy, aryloxy or amino; aralkyl or cycloalkyl; or aryl, which is unsubstituted or substituted by —C$_n$H$_{2n+1}$ or —OC$_n$H$_{2n+1}$, in which n is an integer from 1 to 5, or halogen, acylamino, —SO$_3$H, —SO$_2$NH$_2$ or N-substituted or N,N-disubstituted sulphonamide, —COOH, carboxamido groups, carbalkoxy groups, phenoxycarbonyl, benzyloxycarbonyl, hydroxyl, nitro, cyano or amino groups, alkylmercapto or —SO$_2$—E or —CO—E, in which E is alkyl having 1 to 18 carbon atoms, which is unsubstituted or substituted by halogen, nitro, cyano, amino or alkoxy having 1 to 18 carbon atoms; or E is also cycloalkyl, aryl, pyridyl, pyrimidyl, furyl or thienyl, and M is also pyridyl, furyl, thienyl or perfluoroalkyl or, if Z is —CO—, amino, mono- or di-alkylamino having up to 5 carbon atoms in the alkyl moiety, alkoxy having 1 to 18 carbon atoms, acyl, carbalkoxy having 1 to 5 carbon atoms in the alkoxy moiety, or carboxamido which is N-substituted or N,N-disubstituted by alkyl having 1 to 3 carbon atoms and/or by phenyl.

Further materials, for colour photography, which are particularly suitable are those which contain, as yellow couplers, compounds of the formula

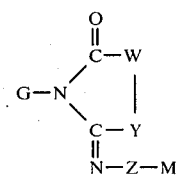

(2)

in which G, Z and M are as defined and —W—Y— is of the formulae

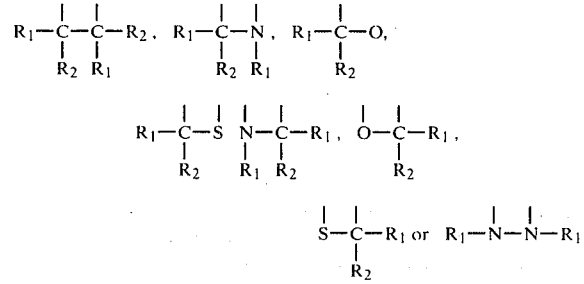

in which R$_1$ is hydrogen, alkyl having 1 to 18 carbon atoms, aralkyl, cycloalkyl, aryl or acyl having 1 to 5 carbon atoms and R$_2$ is alkyl having 1 to 18 carbon atoms, aralkyl or aryl, and R$_1$ and R$_2$ together with the atom or atoms to which they are bonded can form a 4-membered to 6-membered ring, or compounds of the formula

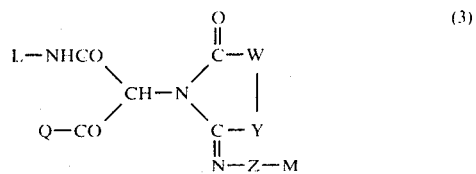

(3)

in which M, —W—Y— and Z are as defined, L is phenyl which is unsubstituted or substituted by halogen, alkyl, alkoxy, acylamino or sulphonamide, carboxamide or carboxylic acid ester groups and Q is alkyl having 1 to 32 carbon atoms, α-alkoxyalkyl having 2 to 32 carbon atoms, α-aryloxyalkyl having 7 to 40 carbon atoms, cycloalkyl having 1 to 4 cycloalkyl rings or an aryl or heterocyclic radical which is unsubstituted or substituted by alkyl or alkoxy, each having 1 to 18 carbon atoms, halogen, acylamino or sulphonic acid or carboxamide groups, Preferred representative of the compounds of the formula (3) are those of the formula

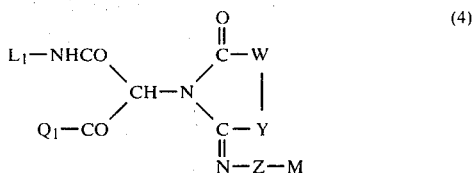

(4)

in which M, —W—Y— and Z are as defined, L$_1$ is phenyl which is unsubstituted or substituted by chlorine, alkoxy having 1 to 5 carbon atoms, aliphatic acylamino having 1 to 40 carbon atoms, carboxamido having 1 to 40 carbon atoms, which is unsubstituted, N-substituted or N,N-disubstituted, or carboxylic acid ester groups having 2 to 40 carbon atoms, it being possible for the —CONH— and —NHCO— groups to carry groups conferring solubility in oil, and Q$_1$ is tert.-butyl, norbornyl, 2,2,2-bicyclooctyl, phenyl, 3,4-methylenedioxyphenyl, p-methoxyphenyl or 3-acylaminophenyl, in which the acylamino group carries a radical conferring solubility in oil, and those of the formula

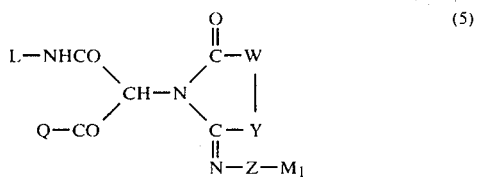

(5)

in which L, Q, —W—Y— and Z are as defined and M$_1$ is alkyl having 1 to 10 carbon atoms, which is unsubstituted or substituted by alkoxy having 1 to 5 carbon atoms or phenoxy; benzyl or phenyl which is unsubstituted or substituted by alkyl or alkoxy having 1 to 5 carbon atoms or halogen, such as chlorine or bromine, or acylamino; cyclohexyl, norbornyl, adamantyl or, if Z is —CO—, alkoxy having 1 to 5 carbon atoms or mono-dialkylamino having 1 to 5 carbon atoms in the alkyl moiety.

Further materials, for colour photography, which are particularly preferred are those which contain, as yellow couplers, compounds of the formula

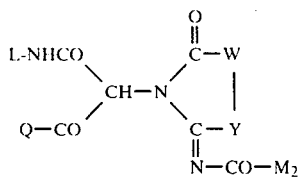
(6)

in which L, Q and —W—Y— are as defined and $M_2$ is alkyl having 1 to 10 carbon atoms, which is unsubstituted or substituted by alkoxy having 1 to 5 carbon atoms or phenoxy; alkoxy having 1 to 5 carbon atoms; benzyl; phenyl which is unsubstituted or substituted by alkyl or alkoxy having 1 to 5 carbon atoms or chlorine, or mono- or di-alkylamino having 1 to 5 carbon atoms in the alkyl moiety, or of the formula

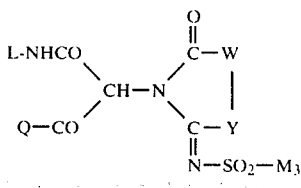
(7)

in which L, Q and —W—Y— are as defined and $M_3$ is alkyl having 1 to 5 carbon atoms, or phenyl which is unsubstituted or substituted by alkyl having 1 to 5 carbon atoms, chlorine or acylamino having 1 to 5 carbon atoms.

Finally, particularly valuable materials for colour photography are also those which contain, as yellow couplers, compounds of the formula

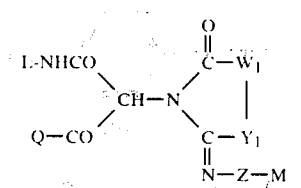
(8)

in which L, M, Q and Z are as defined and $-W_1-Y_1-$ is of the formulae

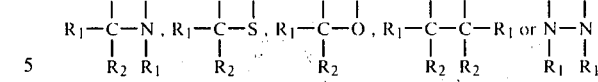

in which $R_1$ is hydrogen, alkyl having 1 to 18 carbon atoms, aralkyl, cycloalkyl, aryl, especially phenyl, or acyl having 1 to 5 carbon atoms and $R_2$ is alkyl having 1 to 18 carbon atoms, aralkyl or aryl, especially phenyl, and $R_1$ and $R_2$ together with the atom or atoms to which they are bonded can form a 4-membered to 6-membered ring; or especially materials, for colour photography, which contain, as yellow couplers, compounds of the formula

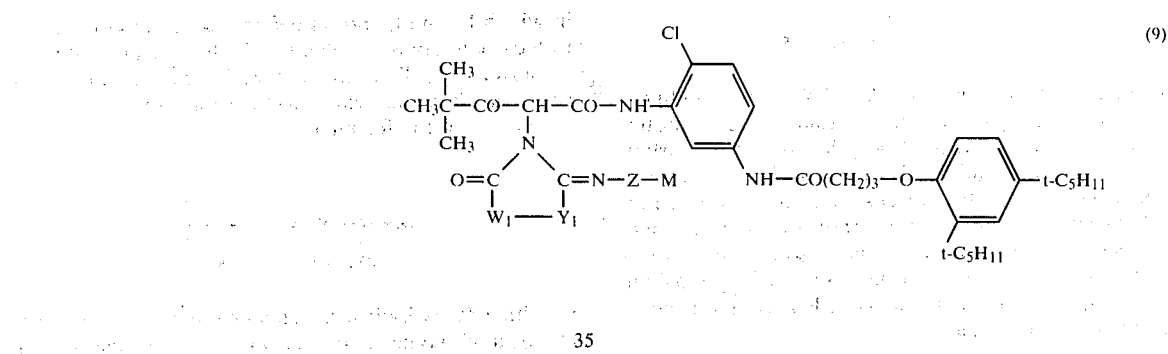
(9)

in which Z, M and $-W_1-Y_1-$ are as defined; or materials, for colour photography, which contain, as yellow couplers, compounds of the formula

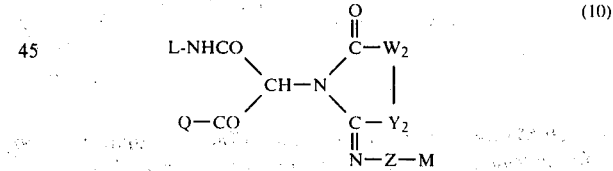
(10)

in which L, M, Q and Z are as defined and $-W_2-Y_2-$ is of the formulae

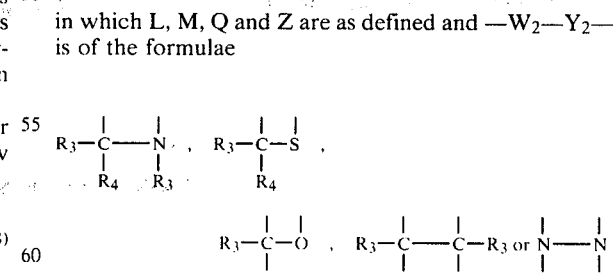

in which $R_3$ is hydrogen, alkyl having 1 to 5 carbon atoms, acyl having 1 to 5 carbon atoms or phenyl and $R_4$ is alkyl having 1 to 5 carbon atoms or phenyl; or especially materials, for colour photography, which contain, as yellow couplers, compounds of the formula

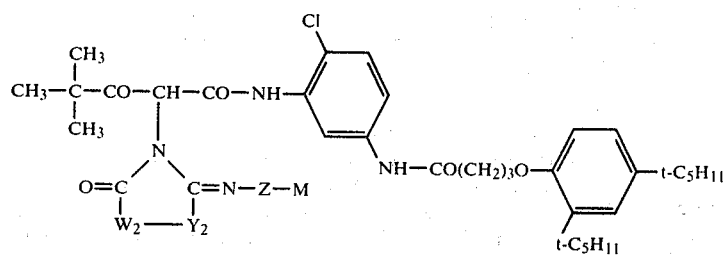
(11)

in which Z, M and —$W_2$—$Y_2$— are as defined; or materials, for colour photography, which contain, as yellow couplers, compounds of the formula

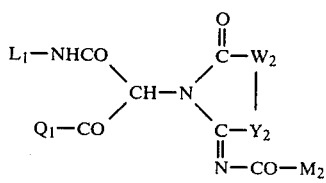
(12)

in which $L_1$ and $Q_1$ and also —$W_2$—$Y_2$— are as defined, $M_2$ is alkyl having 1 to 10 carbon atoms, which is unsubstituted or substituted by alkoxy having 1 to 5 carbon atoms or phenoxy; alkoxy having 1 to 5 carbon atoms; benzyl; phenyl which is unsubstituted or substituted by alkyl or alkoxy having 1 to 5 carbon atoms or chlorine, or mono- or di-alkylamino having 1 to 5 carbon atoms in the alkyl moiety; or especially materials, for colour photography, which contain, as yellow couplers, compounds of the formula

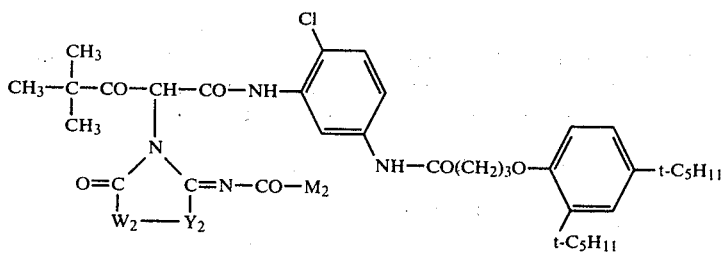
(13)

in which $M_2$ and —$W_2$—$Y_2$— are as defined; or materials, for colour photography, which contain, as yellow couplers, compounds of the formula

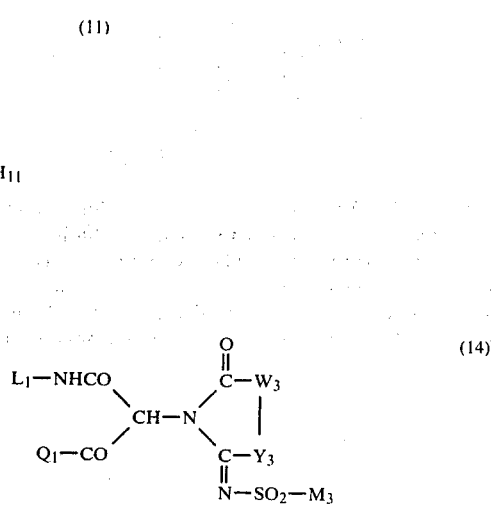
(14)

in which $L_1$ and $Q_1$ are as defined, $M_3$ is alkyl having 1 to 5 carbon atoms, or phenyl which is unsubstituted or substituted by alkyl having 1 to 5 carbon atoms, chlorine or acylamino having 1 to 5 carbon atoms, and —$W_3$—$Y_3$— is of the formula

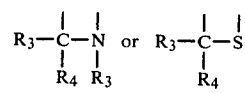

in which $R_3$ is hydrogen, alkyl having 1 to 5 carbon atoms, acyl having 1 to 5 carbon atoms or phenyl and $R_4$ is alkyl having 1 to 5 carbon atoms or phenyl; or especially materials, for colour photography, which contain, as yellow couplers, compounds of the formula

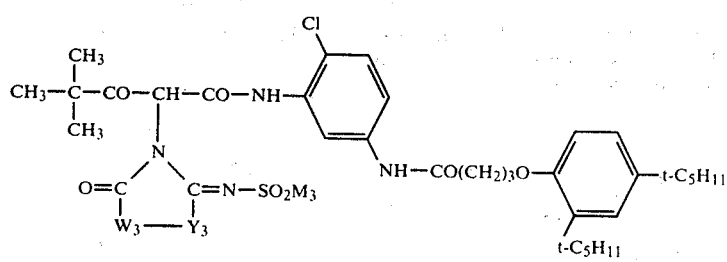
(15)

in which $M_3$ and —$W_3$—$Y_3$— are as defined.

Very particularly preferred materials, for colour photography, are those which contain, as yellow couplers, compounds of the formula

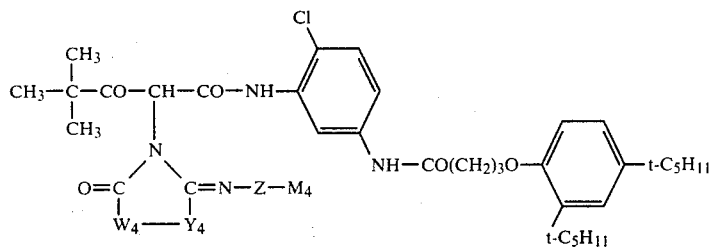
(16)

in which Z is —CO— or —SO₂— and M₄ is alkyl having 1 to 5 carbon atoms, benzyl, phenyl, which is unsubstituted or substituted by alkyl having 1 to 3 carbon atoms, chlorine and/or nitro, or, if Z is —CO—, alkoxy having 2 to 5 carbon atoms, monoalkylamino having 1 to 5 carbon atoms, carbalkoxy having 1 to 3 carbon atoms in the alkoxy moiety or carboxamide which is N-substituted or N,N-disubstituted by alkyl having 1 to 3 carbon atoms and/or by phenyl, and —W₄—Y₄— is of the formulae

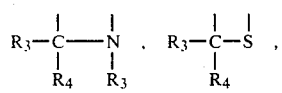

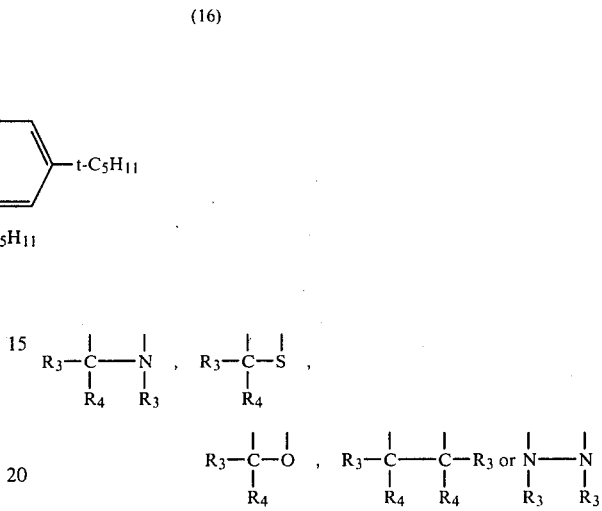

in which $R_3$ is hydrogen, alkyl having 1 to 5 carbon atoms, acyl having 2 to 5 carbon atoms or phenyl and $R_4$ is alkyl having 1 to 5 carbon atoms or phenyl, or contain yellow couplers of the formula

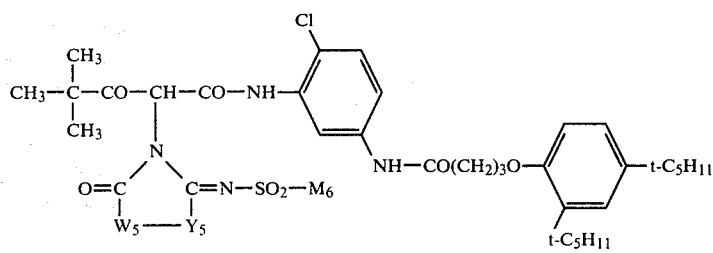
(18)

in which $M_6$ is alkyl having 1 to 3 carbon atoms or phenyl which is unsubstituted or substituted by alkyl having 1 to 3 carbon atoms, and —W₅—Y₅— is of the formula

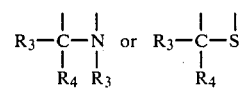

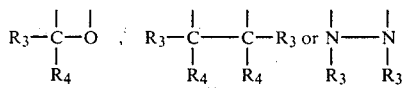

in which $R_3$ is hydrogen, alkyl having 1 to 5 carbon atoms, acyl having 2 to 5 carbon atoms or phenyl and $R_4$ is alkyl having 1 to 5 carbon atoms or phenyl, or contain yellow couplers of the formula

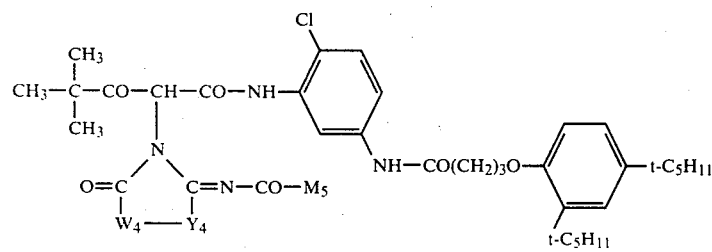
(17)

in which $M_5$ is alkyl having 1 to 5 carbon atoms, alkoxy having 2 to 5 carbon atoms, benzyl, phenyl which is unsubstituted or substituted by chlorine or nitro, monoalkylamino having 1 to 5 carbon atoms, carbalkoxy having 1 to 3 carbon atoms in the alkoxy moiety or carboxamido which is N-substituted or N,N-disubstituted by alkyl having 1 to 3 carbon atoms and/or phenyl, and —W₄—Y₄— is of the formulae in which $R_3$ is hydrogen, alkyl having 1 to 5 carbon atoms, acyl having 2 to 5 carbon atoms or phenyl and $R_4$ is alkyl having 1 to 5 carbon atoms or phenyl.

The leaving groups of the formula

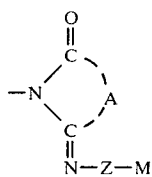

(19)

in which A, M and Z are as defined, can be reacted, employing various known processes, to give the yellow coupler molecule.

In general, the leaving groups are reacted in their protonated form in an inert solvent, for example acetonitrile, dimethylformamide, dimethylsulphoxide or carbon tetrachloride, in the presence of a base, for example sodium hydroxide, potassium hydroxide or symmetrical collidine, with a compound of the general formula

G-X    (20)

in which G is the radical, which has already been defined, of a yellow coupler and X is a chlorine or bromine atom.

However, it is also possible first to prepare a salt, preferably the potassium or silver salt, of the leaving group and to react this with the compound G-X in an inert solvent.

The azeniate ion, which first also forms from the leaving group and the acid-binding agent (base), has the formula given below, to which a corresponding mesomeric limiting formula can be assigned:

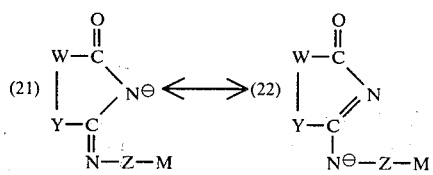

In accordance with the relative electron density on the two nitrogen atoms participating in mesomerism, which, in turn, is of course dependent on W and Y and -Z-M, the reaction with the reactant G-Cl or G-Br can now take place either on the ring nitrogen or on the exocyclic nitrogen. The corresponding isomeric compounds then form. This behaviour has been described in the literature in the case of other mesomeric educts and for ambidentate anions (in this context c.f., for example, R. Gompper, Angew. Chem. 76, 412 [1964]).

It has also been found that, in the case of the category of compounds examined, this isomerism (if it occurs at all) has no influence on the desired properties in use. For this reason, a detailed description of the isomeric forms possible in each case is not given. However, it can be assumed that the isomeric forms which are possible can be used for the desired application.

The acylaminolactams of the formulae (21) and (22) used as leaving groups can be prepared by known methods.

In general, the procedure is to react an amine of the formula (23) with an acid halide, preferably an acid chloride, in the presence of an acid-binding agent, or to allow the amino compound to react with an acid anhydride in the conventional manner:

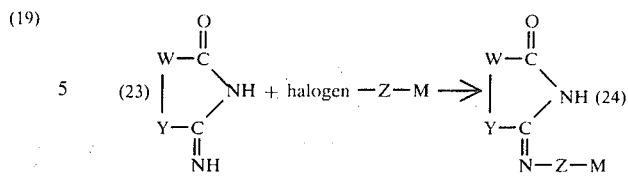

However, it is also possible to prepare the acylaminolactams by cyclisation of a compound which is already acylated, as is described, for example, in Monatshefte für Chemie, Volume 101, 344 (1970).

The amino-lactams of the formula (23) are obtained by methods such as are described, for example, in Beilstein 27, H 233; Tetrahedron 23, 4539 (1967); Ber. 46, 2077 (1913); Monatshefte Chemie 101, 344 (1970); J. Chem. Soc. 1930, 2374; Netherlands Patent Application 6,409,475 and FR-M 4119.

The acid halides, in which Z is a —CO group, are derived, for example, from the following carboxylic acids and carboxylic acid derivatives: acetic acid, formic acid, propionic acid, butyric acid, isobutyric acid, 2-methylbutyric acid, valeric acid, isovaleric acid, caproic acid, caprylic acid, capric acid, dodecanoic acid, tetradecanoic acid, palmitic acid, stearic acid, cyclohexanecarboxylic acid, pivalic acid, chloroacetic acid, dichloroacetic acid, trichloroacetic acid, methoxyacetic acid, ethoxyacetic acid, phenylacetic acid, phenoxyacetic acid, 2,4-di-t-pentylphenoxyacetic acid, 4-t-pentylphenoxyacetic acid, N,N-dimethylcarbamic acid, monomethyl carbonate, monomethoxyethyl carbonate, monoisopropyl carbonate, monoisobutyl carbonate, monophenyl carbonate, monobenzyl carbonate, mono-t-butyl carbonate, benzoic acid, o-toluic acid, m-toluic acid, p-toluic acid, o-chlorobenzoic acid, m-chlorobenzoic acid, p-chlorobenzoic acid, m-methoxybenzoic acid, p-methoxybenzoic acid, p-bromobenzoic acid, m-dimethylaminobenzoic acid, m-cyanobenzoic acid, p-cyanobenzoic acid, p-methylsulphonylbenzoic acid, m-methylsulphonylbenzoic acid, m-trifluoromethylbenzoic acid, 3,4-dimethylbenzoic acid, 2,4-dimethylbenzoic acid, 3,4-dimethoxybenzoic acid, 3,5-dimethoxybenzoic acid, 2,4-dimethoxybenzoic acid, p-t-butylbenzoic acid, 3,4-dichlorobenzoic acid, 2,4-dichlorobenzoic acid, pyridine-2-carboxylic acid, pyridine-3-carboxylic acid, pyridine-4-carboxylic acid, thiophene-2-carboxylic acid, furane-2-carboxylic acid, naphthalene-1-carboxylic acid, nephthalene-2-carboxylic acid, 4-methoxycarbonylbenzoic acid and 4-ethoxycarbonylbenzoic acid.

The sulphonic acid halides, in which Z is a —SO₂ group, are derived, for example, from the following sulphonic acids: methanesulphonic acid, trifluoromethanesulphonic acid, benzenesulphonic acid, p-acetylaminobenzenesulphonic acid, o- or p-toluenesulphonic acid, xylenesulphonic acid, pyridine-3-sulphonic acid, naphthalene-1-sulphonic acid and naphthalene-2-sulphonic acid.

Amine compounds of the formula (23) which can be employed are, for example, compounds of the following formulae:

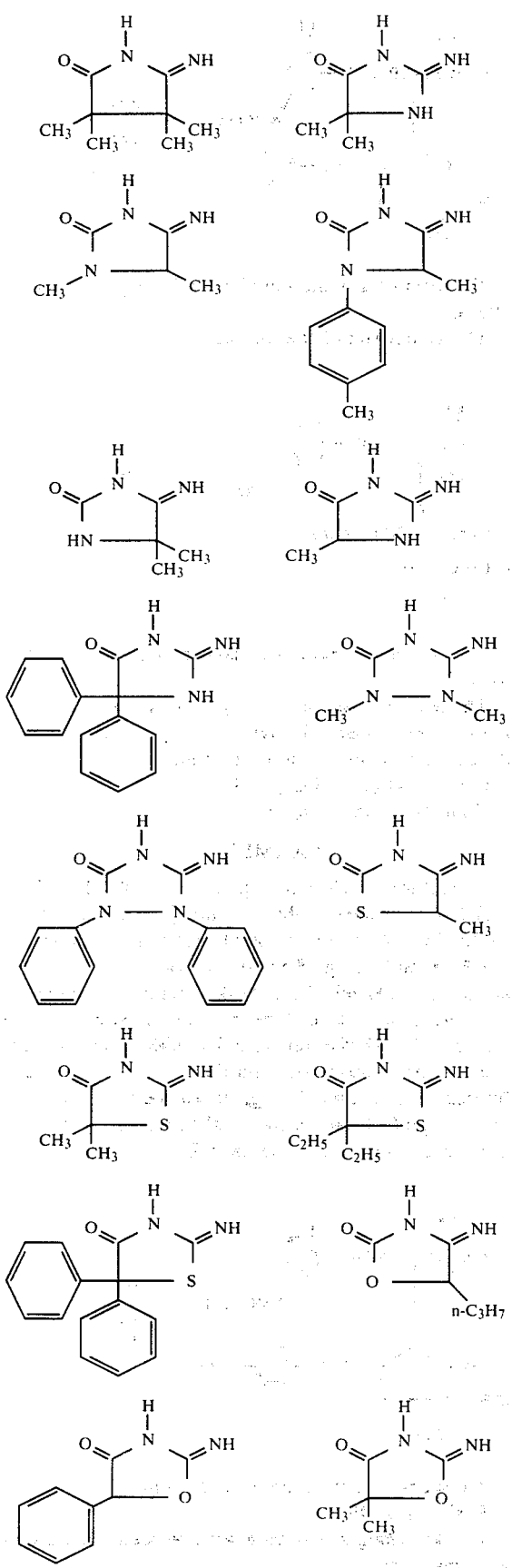

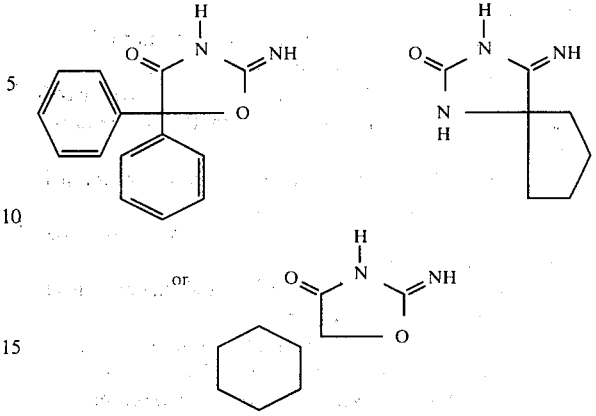

The α-halogeno-acylacetanilides which are known to those skilled in the art and are described, inter alia, in German Offenlegungsschrift No. 2,114,577, French Patent Specifications Nos. 991,453 and 869,169 and U.S. Pat. Nos. 2,728,658 and 3,277,155 can be employed as starting materials of the formulae Cl-G and Br-G for the synthesis of the yellow coupler according to the invention.

Thus, for example, the following compounds can be used:

1. α-Acetyl-α,2-dichloro-5-[α-(2′,4′-di-tert.-amylphenoxy)-acetylamino]-acetanilide
2. α-Pivalyl-α-bromo-2-chloro-5-[α′-tert.-amylphenoxy)-n-tetradecanoylamino]-acetanilide
3. α-(β′-Methoxy-α′,α′-dimethyl-propionyl)-α-chloro-4-[N-(γ″-phenylpropyl)-N-(p-tolyl)carbamoylmethoxy]-acetanilide.
4. α-(α′-Methoxyisobutyryl)-α-chloro-2-methoxy-5-[Γ-(3″-n-pentadecylphenoxy)-butyramino]-acetanilide
5. α-(α′-Phenoxyisobutyryl)-α,2-dichloro-5-(n-octadecylsuccinimido)-acetanilide
6. 1-[α-(α′α′-Dimethylbutyryl)-α-chloro-acetylamino]-2-phenoxybenzene-5-carboxylic acid (di-n-butoxy)-phosphono-ethylamide [—CO—NH—CH$_2$—CH$_2$—(OP)(O—C$_4$H$_9$)$_2$]
7. α-(α′,α′-Dimethyl-octadecanoyl)-α-bromo-3,5-bis-methoxycarbonyl-acetanilide
8. α-(α′-Ethyl-α′-methyl-hexanoyl)-α-bromo-2-chloro-5-[γ″-(2″,4″-di-tert.-amylphenoxy)-butyroamino]-acetanilide
9. α-(α′,α′,γ′,γ′-Tetramethyl-valeryl)-α,2-dichloro-5-(n-dodecyloxycarbonyl)-acetanilide
10. α-(1′-Methyl-cyclohexanecarbonyl)-α-bromo-2-chloro-5-[α″-(2″,4″-di-tert.-amylphenoxy)-butyroamino]-acetanilide
11. α-(7′,7′-Dimethylnorbornane-1′-carbonyl)-α,2-dichloro-5-[α″-(2″,4″-di-tert.-amylphenoxy)-acetamino]-acetanilide
12. α-Benzoyl-α-chloro-2-methoxy-5-[α′-(3′-n-dodecyloxyphenoxy)-butyroamino]-acetanilide
13. 1-[α-(4′-Methoxybenzoyl)-α-chloro]-acetylamino-2-chloro-5-[β-(N-palmityl-N-n-butyl-amino)-propionylamino]-benzene
14. α-Piperonyloyl-α,2-dichloro-5-(α′-phenoxy-n-tetradecanoylamino)-acetanilide
15. (α′-n-Dodecyloxycarbonyl)-ethyl 1-[α-(2′-chlorobenzoyl)-α-chloro]-acetylaminobenzene-4-carboxylate 16. α-(4′-Chlorobenzoyl)-α-bromo-2-hexadecyloxy-acetanilide
17. α-Piperonyloyl-α-chloro-3-[(N-methyl-N-n-octadecyl)-sulphamoyl]-acetanilide
18. α-{3′-[γ-(2″,4″-Di-t-amylphenoxy)-butyroamino]-benzoyl}-α-bromo-4-chloro-2,5-dimethoxy-acetanilide
19. α-{3′-[α″-(3″-n-pentadecylphenoxy)-butyroamino]-benzoyl}-α,2-dichloro-acetanilide
20. α-(4′-n-Hexadecyloxy-benzoyl)-α-chloro-2-methoxy-acetanilide
21. α-Pivaloyl-α,2-dichloro-5-[γ′-(2′,4′-di-tert.-amylphenoxy)butyroaminoacetanilide.

The yellow couplers according to the invention are a category of compounds which is novel per se. They are distinguished by high reactivity (high maximum density), minimal fog, high fastness to light, both of the couplers and of the dyes formed, and excellent spectral properties of the dyes formed.

The colour couplers of the formulae (1) to (18), which are also a subject of the present invention, can be incorporated in a known manner into photographic layers, for example silver halide emulsions containing gelatine or binders.

For example, they can be used with silver bromide, silver chloride or silver iodide emulsions or with those emulsions which contain a mixture of silver halides, such as silver bromide/iodide or silver chloride/bromide emulsions.

The emulsions can be chemically sensitised and can also contain conventional organic stabilisers and antifogging agents, as well as conventional plasticizers, for example glycerol. The emulsions can also be hardened with the hardeners customary for gelatine. Furthermore, the emulsions can contain conventional coating auxiliaries. The emulsions can be applied to conventional layer supports for photographic recording material. If desired, a mixture of several colloids can be used to disperse the silver halides.

The conventional developing baths can be used to develop the recording material for colour photography. These baths as a rule contain a developer substance of the p-phenylenediamine type, a development retardant, such as potassium bromide, an antioxidant, such as sodium sulphite, and a base, for example an alkali metal hydroxide or alkali metal carbonate. Furthermore, the developing baths can contain a conventional antifogging agent and complex-forming agent.

Corresponding possible applications are described, for example, in U.S. Pat. Nos. 2,304,939, 2,304,940, 2,322,027, 2,284,879, 2,801,170, 2,801,171, 2,749,360 and 2,825,382.

EXAMPLE 1

A mixture of 1.8 g of α-pivaloyl-α,2-dichloro-5-[γ-(2,4-di-tert.-amylphenoxy)-butyroamino]-acetanilide, 0.8 g of 5,5-diethyl-2-benzoylimino-1,3-thiazolidin-4-one and 0.26 g of powdered potassium hydroxide in 10 ml of dimethylformamide are stirred at room temperature for 3 hours. The reaction mixture is then added to 200 ml of water (acidified with 1 ml of concentrated hydrochloric acid) and the precipitate formed is filtered off with suction and, after drying, recrystallised from a mixture of 10 ml of ethyl acetate and 40 ml of petroleum ether.

This gives 1.2 g of the compound of the formula

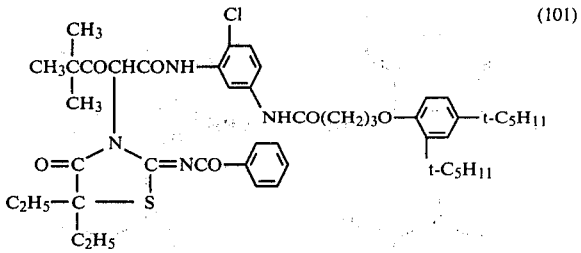

(101)

in the form of a white powder. Melting point: 104° to 106° C.

The compound of the formula

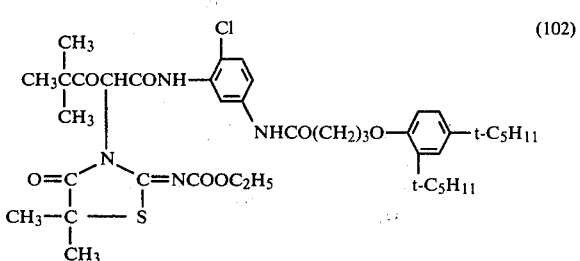

(102)

is prepared in an analogous manner. Melting point: 98° to 100° C.

The maximum density ($D_{max}$) in this example and in the examples which follow was determined in accordance with the instructions in Example 5.

Compound (101): $D_{max}$: 0.95
Compound (102): $D_{max}$: 1.31

EXAMPLE 2

A mixture of 1.8 g of α-pivaloyl-α,2-dichloro-5-[γ-(2,4-di-t-amylphenoxy)-butyroamino]-acetanilide, 1.4 g of 5,5-diethyl-2-(p-toluenesulphonylimino)-1,3-thiazolidin-4-one and 0.26 g of powdered potassium hydroxide are stirred in 10 ml of dimethylformamide for 24 hours at room temperature. The reaction mixture is then added to 200 ml of water (acidified with 1 ml of concentrated hydrochloric acid) and the precipitate formed is filtered off and, after drying, chromatographed on 50 g of silica gel (solvent: benzene/ethyl acetate, 17:3). This gives the compound of the formula

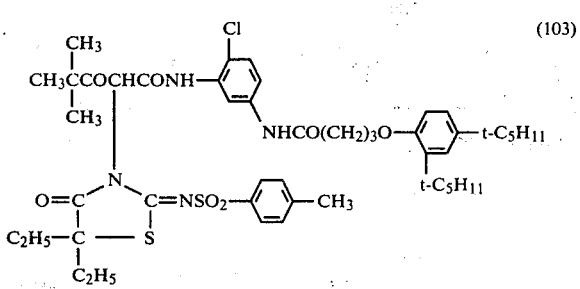

(103)

in the form of a white powder. Melting point: 108° to 111° C. $D_{max}$: 0.98

The following compounds are prepared in an analogous manner:

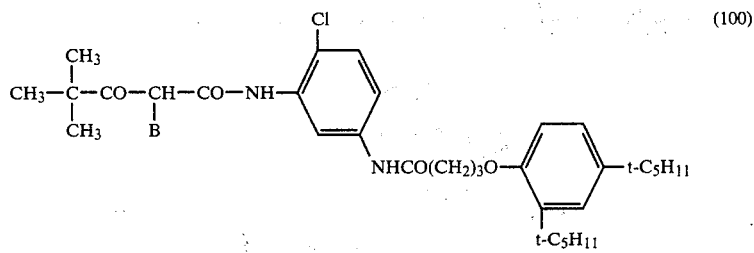

(100)

TABLE 1

| No. | B | Melting point °C. | $D_{max}$ |
|---|---|---|---|
| 104 | (structure) | 165–167 | 1.12 |
| 105 | (structure) | 102–107 | 1.47 |
| 106 | (structure) | 100–103 | 1.00 |
| 107 | (structure) | 97–104 | 0.85 |
| 108 | (structure) | 109–111 | 1.10 |

EXAMPLE 3

A mixture of 1.8 g of α-pivaloyl-α,2-dichloro-5-[γ-(2,4-di-t-amyl-phenoxy)-butyroamino]-acetanilide, 1.0 g of 5,5-dimethyl-2-pivaloylimino-1,3-thiazolidin-4-one and 0.3 g of powdered potassium hydroxide in 25 ml of acetonitrile are refluxed for 13 hours. The mixture is then filtered and the filtrate is evaporated. After chromatography on 40 g of silica gel, 0.35 g of the coupler of the formula

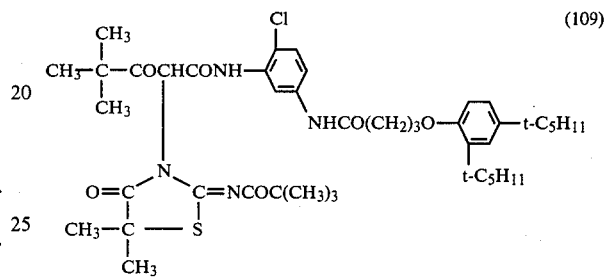

(109)

is obtained in the form of a light yellow powder. Melting point: 90° to 95° C. $D_{max}$: 1.25

The compounds of Table 2 (general formula 100) are prepared in an analogous manner.

TABLE 2

| No. | B | Melting point °C. | $D_{max}$ |
|---|---|---|---|
| 110 | (structure) | 99–101 | 1.22 |
| 111 | (structure) | 159–161 | 0.77 |
| 112 | (structure) | 111–122 | 0.92 |
| 113 | (structure) | 103–106 | 0.45 |
| 114 | (structure) | 114–118 | 1.34 |
| 115 | (structure) | 104–110 | 1.35 |

TABLE 2-continued

| No. | B | Melting point °C. | $D_{max}$ |
|---|---|---|---|
| 116 | | 206–207 | 1.05 |
| 117 | | 112–119 | 1.07 |
| 118 | | 130–134 | 0.97 |
| 119 | | 164–165 | 1.15 |
| 120 | | 130–135 | 1.21 |
| 121 | | 115–118 | 1.32 |
| 122 | | 111–112 | 1.10 |

TABLE 2-continued

| No. | B | Melting point °C. | $D_{max}$ |
|---|---|---|---|
| 123 | | 190–192 | 0.98 |
| 124 | | 134–137 | 1.21 |
| 125 | | 116–119 | 1.62 |

EXAMPLE 4

A mixture of 1.8 g of α-pivaloyl-α,2-dichloro-5-[γ-(2,4-di-t-amylphenoxy)-butyroamino]-acetanilide, 1.6 g of 5,5-diphenyl-2-(p-toluenesulphonylimino)-imidazolidin-4-one and 0.9 g of triethylamine in 30 ml of acetonitrile are refluxed for 3 hours. The mixture is then filtered, the filtrate is evaporated and the residue thus obtained is chromatographed on 40 g of silica gel. This gives 2.4 g of the compound of the formula

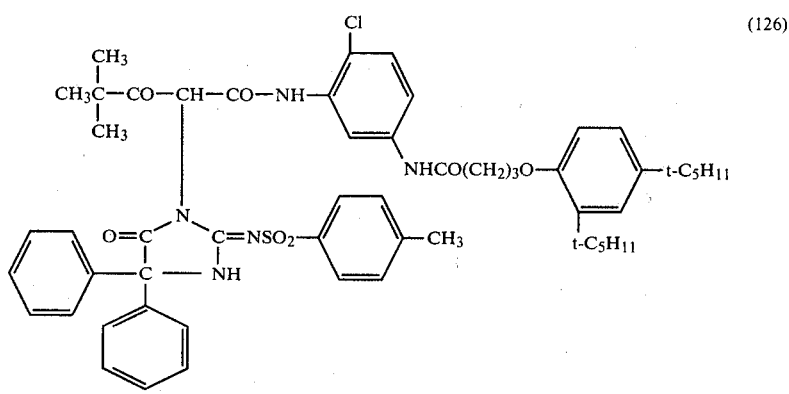
(126)

in the form of a yellowish powder. Melting point: 116° to 122° C. $D_{max}$: 1.34

The compounds of Table 3 (general formula 100) are prepared in an analogous manner.

TABLE 3

| No. | B | Melting point °C. | $D_{max}$ |
|---|---|---|---|
| 127 | 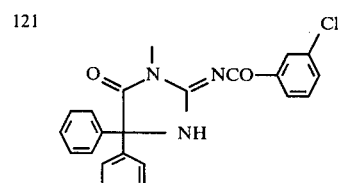 | 103–108 | 0.92 |

TABLE 3-continued

| No. | B | Melting point °C. | $D_{max}$ |
|---|---|---|---|
| 128 | 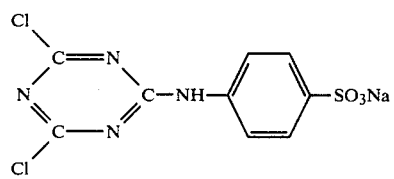 | 206-209 | 1.05 |

EXAMPLE 5

0.1 mmol of the yellow coupler of the formula (105), the preparation of which has been described in Example 2, is dissolved in 2.0 ml of tricresyl phosphate/methylene chloride (1:9). The methylene chloride is evaporated off, 2.0 ml of an 8% strength aqueous solution of sodium isopropylnaphthalenesulphonate, 6.6 ml of a 6% strength gelatine solution and 1.2 ml of water are added, the pH of the mixture is adjusted to 6.5 and the mixture is emulsified for 5 minutes with the aid of an ultrasonic apparatus, with a power of 100 watts.

2.5 ml of the coupler emulsion, which has been freshly exposed to ultrasonic sound, 1.6 ml of a silver bromide emulsion having a pH of 6.5 and containing 1.4% of silver and 6.0% of gelatine, 1.0 ml of a 1% strength aqueous solution of the hardener of the formula

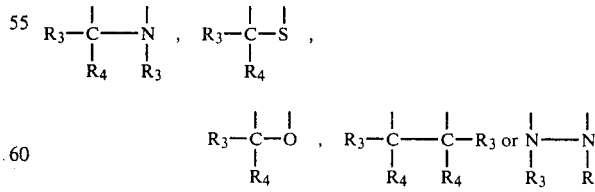

(129)

and 5.0 ml of water are mixed together and coated at 40° C. onto a substrated 13 cm × 18 cm glass plate.

After the coating has solidified at 10° C., the plate is dried in a drying cabinet with circulating air, at room temperature.

A strip, cut to 4.0 cm × 6.5 cm, is exposed under a step wedge for 2 seconds with 500 Lux and then treated at 24° C. as follows:

| | Minutes |
|---|---|
| 1. Colour developing | 5 |
| 2. Washing | 5 |
| 3. First fixing | 2 |
| 4. Washing | 2 |
| 5. Silver bleaching | 4 |
| 6. Washing | 2 |
| 7. Second fixing | 4 |
| 8. Washing | 10 |
| 9. Drying | 10 |

A colour developer of the following composition is used for processing:

| | | |
|---|---|---|
| 4-Amino-3-methyl-N-ethyl-N-[β-(methyl-sulphonamido)-ethyl]-aniline . 1½ $H_2SO_4$ . $H_2O$ | 10 | mmol/l |
| Anhydrous sodium sulphite | 2.0 | g/l |
| Potassium bromide | 0.5 | g/l |
| Potassium carbonate | 40.0 | g/l |
| Benzyl alcohol | 10.0 | ml/l |
| (pH: 10.7) | | |

Conventional baths are used for fixing and silver bleaching.

A clear sharp yellow wedge with an absorption maximum at 444 nm and a maximum density $D_{max}=1.47$ is obtained in the manner described above.

What is claimed is:

1. A yellow coupler of the formula

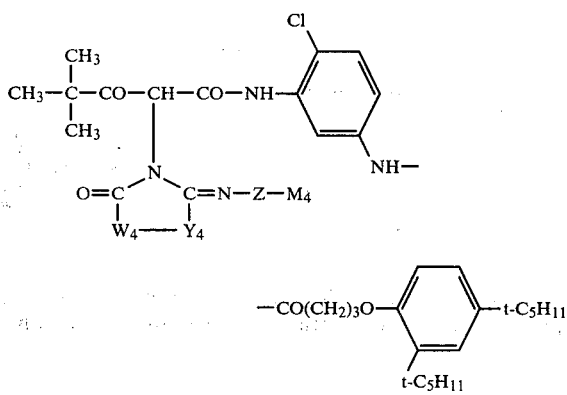

in which Z is —CO— or —$SO_2$— and $M_4$ is alkyl having 1 to 5 carbon atoms, benzyl, phenyl, which is unsubstituted or substituted by alkyl having 1 to 3 carbon atoms, chlorine and/or nitro, or, if Z is —CO—, alkoxy having 2 to 5 carbon atoms, monoalkylamino having 1 to 5 carbon atoms, carbalkoxy having 1 to 3 carbon atoms in the alkoxy moiety or carboxamido which is N-substituted or N,N-disubstituted by alkyl having 1 to 3 carbon atoms and/or by phenyl, and —$W_4$—$Y_4$— is the formulae $$R_3-\underset{R_4}{\overset{|}{C}}-\underset{R_3}{\overset{|}{N}}\;,\;\;R_3-\underset{R_4}{\overset{|}{C}}-S\;,$$

$$R_3-\underset{R_4}{\overset{|}{C}}-O\;,\;\;R_3-\underset{R_4}{\overset{|}{C}}-\underset{R_4}{\overset{|}{C}}-R_3\;\text{or}\;N-\underset{R_3}{\overset{|}{\phantom{C}}}-\underset{R_3}{\overset{|}{N}}$$

in which $R_3$ is hydrogen, alkyl having 1 to 5 carbon atoms, acyl having 2 to 5 carbon atoms or phenyl and $R_4$ is alkyl having 1 to 5 carbon atoms or phenyl.

2. A yellow coupler according to claim 1, which is of the formula

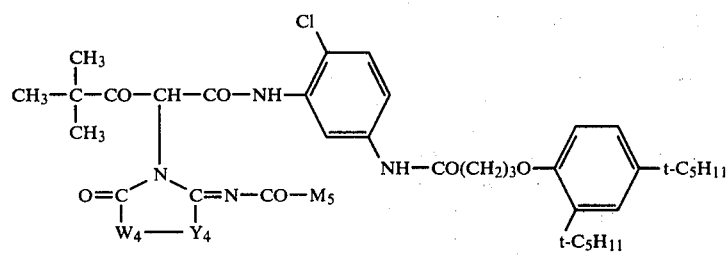

in which $M_5$ is alkyl having 1 to 5 carbon atoms, alkoxy having 2 to 5 carbon atoms, benzyl, phenyl which is unsubstituted or substituted by chlorine or nitro, monoalkylamino having 1 to 5 carbon atoms, carbalkoxy having 1 to 3 carbon atoms in the alkoxy moiety or carboxamido which is N-substituted or N,N-disubstituted by alkyl having 1 to 3 carbon atoms and/or phenyl, and —$W_4$—$Y_4$— is as defined in claim 1.

3. A yellow coupler according to claim 1, which is of the formula

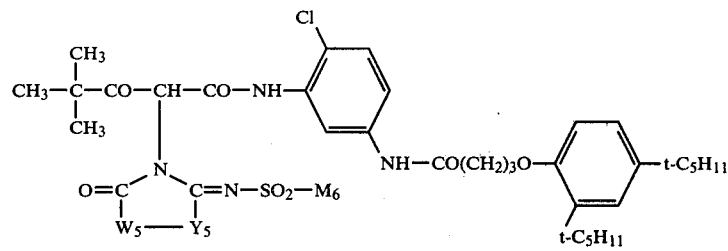

in which $M_6$ is alkyl having 1 to 3 carbon atoms or phenyl which is unsubstituted or substituted by alkyl having 1 to 3 carbon atoms, and —$W_5$—$Y_5$— is of the formula

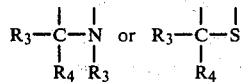

in which $R_3$ is hydrogen, alkyl having 1 to 5 carbon atoms, acyl having 2 to 5 carbon atoms or phenyl and $R_4$ is alkyl having 1 to 5 carbon atoms or phenyl.

* * * * *

UNITED STATES PATENT AND TRADEMARK OFFICE
CERTIFICATE OF CORRECTION

PATENT NO. : 4,324,898
DATED : April 13, 1982
INVENTOR(S) : Paul Tschopp

It is certified that error appears in the above-identified patent and that said Letters Patent are hereby corrected as shown below:

| | |
|---|---|
| Col. 2, line 10 | Insert --(German Offenlegungsschrift 1,800,420)-- |
| Col. 2, line 11 | Delete "-SCH" and insert -- -SCN-- |
| Col. 2, line 25 | Insert --(German Offenlegungsschriften 2,163,812, 2,213,461, 2057,941, 2,261,361, 2,431,480 and 2,219,917-- |
| Col. 2, line 35 | Insert --(German Offenlegungsschrift 2,329,587)-- |
| Col. 2, line 45 | Insert --(German Offenlegungsshrift 2,433,812)-- |
| Col. 5, line 45 | Delete "carboxamide" and insert --carboxamido-- |
| Col. 7, line 62 | Insert space between "acyl" and "having" |
| Col. 8, line 21 | Delete "representative" and insert --representatives-- |
| Col. 13, line 19 | Delete "carboxamide" and insert --carboxamido-- |
| Col. 13, line 61 | Insert space between "$M_5$" and "is" |
| Col. 18, line 32 | After "[a'-" insert --(4'-- |
| Col. 18, line 37 | After "5-[" delete "$\Gamma$" and insert --$\gamma$-- |

Signed and Sealed this

Thirteenth Day of July 1982

[SEAL]

Attest:

GERALD J. MOSSINGHOFF

Attesting Officer      Commissioner of Patents and Trademarks